(12) United States Patent
Klobes et al.

(10) Patent No.: US 9,079,833 B2
(45) Date of Patent: Jul. 14, 2015

(54) PROCESS FOR THE PREPARATION OF A POLYSULFIDE

(75) Inventors: Olaf Klobes, Greiz (DE); Jing He, Shanghai (CN)

(73) Assignees: SHANGHAI ICI RESEARCH & DEVELOPMENT & MANAGEMENT CO. LTD., Shanghai (CN); AKZO NOBEL CHEMICALS INTERNATIONAL B.V., Amersfoort (NL)

( * ) Notice: Subject to any disclaimer, the term of this patent is extended or adjusted under 35 U.S.C. 154(b) by 0 days.

(21) Appl. No.: 14/009,897

(22) PCT Filed: Apr. 10, 2012

(86) PCT No.: PCT/EP2012/056389
§ 371 (c)(1),
(2), (4) Date: Oct. 4, 2013

(87) PCT Pub. No.: WO2012/139984
PCT Pub. Date: Oct. 18, 2012

(65) Prior Publication Data
US 2014/0046097 A1   Feb. 13, 2014

Related U.S. Application Data

(60) Provisional application No. 61/512,060, filed on Jul. 27, 2011.

(30) Foreign Application Priority Data

Apr. 12, 2011  (WO) ............... PCT/CN2011/072661
Jul. 27, 2011  (EP) ................................. 11175485

(51) Int. Cl.
C08G 75/02      (2006.01)
C07C 319/24     (2006.01)
C08G 75/14      (2006.01)

(52) U.S. Cl.
CPC ............. *C07C 319/24* (2013.01); *C08G 75/14* (2013.01)

(58) Field of Classification Search
USPC .......................................... 528/373, 374, 375
See application file for complete search history.

(56) References Cited

U.S. PATENT DOCUMENTS

| | | |
|---|---|---|
| 3,499,864 A | 3/1970 | Millen |
| 3,770,678 A | 11/1973 | Paul |
| 3,810,857 A | 5/1974 | Garrigues |
| 3,965,067 A | 6/1976 | Jin |
| 3,968,077 A | 7/1976 | Hwa et al. |
| 4,623,711 A | 11/1986 | Morris et al. |
| 5,206,439 A | 4/1993 | Shaw |
| 5,218,147 A | 6/1993 | Shaw |
| 5,225,472 A | 7/1993 | Cameron et al. |
| 5,442,123 A | 8/1995 | Arretz et al. |
| 5,464,931 A * | 11/1995 | Shaw et al. ................... 528/389 |
| 5,530,163 A | 6/1996 | Shaw |
| 5,565,517 A | 10/1996 | Efner et al. |
| 5,861,539 A | 1/1999 | Shaw |
| 5,907,064 A | 5/1999 | Shaw |
| 6,051,739 A | 4/2000 | Shaw |
| 6,187,960 B1 | 2/2001 | Shaw |
| 6,242,652 B1 | 6/2001 | Bennett |
| 6,284,926 B1 | 9/2001 | Bennett |
| 6,399,832 B1 | 6/2002 | Bennett |
| 2001/0051751 A1 | 12/2001 | Bennett |
| 2007/0249860 A1 | 10/2007 | Zeitler et al. |

FOREIGN PATENT DOCUMENTS

| | | |
|---|---|---|
| CA | 832049 A | 1/1970 |
| DE | 21 56 824 A1 | 5/1972 |
| DE | 23 63 856 A1 | 7/1975 |
| EP | 0 171 092 A2 | 2/1986 |
| EP | 0 202 420 A1 | 11/1986 |
| EP | 0 424 143 A2 | 4/1991 |
| GB | 1167914 A | 10/1969 |
| GB | 1 307 385 A | 2/1973 |
| GB | 1 325 396 A | 8/1973 |
| JP | 4-1267 A | 1/1992 |
| JP | 4-363325 A | 12/1992 |
| JP | 9-255753 A | 9/1997 |
| JP | 10-120788 A | 5/1998 |
| JP | 11-322931 A | 11/1999 |
| JP | 2002-12765 A | 1/2002 |
| NL | 7509420 A | 2/1976 |
| NL | 7509602 A | 2/1976 |
| WO | WO99/60047 | 11/1999 |
| WO | WO 01/66622 A1 | 9/2001 |

OTHER PUBLICATIONS

Koo; Bulletin of the Korean Chemical Society, 2005; 26,12, 2069-2071.*
European Search Report dated Dec. 27, 2011 for related EP Application No. 11175485.9.
International Search Report and Written Opinion dated Jul. 25, 2012 for related PCT Application No. PCT/EP2012/056389.
English abstract of JP Apr. 1267 A published Jan. 6, 1992.
English abstract of JP 4-363325 A published Dec. 16, 1992.
English abstract of JP 9-255753 A published Sep. 30, 1997.
English abstract of JP 10-120788 A published May 12, 1998.
English abstract of JP 2002-12765 A published Jan. 15, 2002.
English translation of DE 23 63 856 A1 published Jul. 3, 1975.

* cited by examiner

*Primary Examiner* — Sudhakar Katakam
*Assistant Examiner* — Pancham Bakshi
(74) *Attorney, Agent, or Firm* — Sandra B. Weiss

(57) ABSTRACT

Process for the preparation of polysulfide of formula (I) HS—$(CH_2)_n$—O—$(CH_2)_m$—O—$(CH_2)_p$—[S—S—$(CH_2)_n$O—$(CH_2)_m$—O—$(CH2)_p]_q$—SH (I) wherein m is an integer in the range 1 to 4, n and p are integers in the range 1-10, and q is an integer in the range 1-60, by oxidizing a bismercaptodiether compound of formula (II) HS—$(CH_2)_n$—O—$(CH_2)_m$—O—$(CH_2)_p$—SH (II) with elemental sulfur in the presence of a base and a protic solvent. This process has a high selectivity towards linear disulfides.

11 Claims, No Drawings

PROCESS FOR THE PREPARATION OF A POLYSULFIDE

This application is the U.S. National Phase of PCT/EP2012/056389 filed on Apr. 10, 2012 and claims the benefit of U.S. Provisional Application No. 61/512,060 filed on Jul. 27, 2011, International Application No. PCT/CN2011/072661 filed on Apr. 12, 2011 and European Application No. 11175485.9 filed on Jul. 27, 2011, the contents of each of which are incorporated herein by reference.

The present invention relates to a process for the preparation of a polysulfide.

Polysulfides are a class of polymers with alternating chains of several sulfur atoms and hydrocarbons. The general formula for the repeating unit is —[R—S$_x$]$_n$—, where x indicates the number of sulfur atoms, n indicates the number of repeating units and, R is an organic radical. Cured polysulfide polymers are resistant to ageing and weathering, highly elastic from −40 to +120° C., and they offer an outstanding chemical resistance, especially against oil and fuel. Because of their properties, these materials find use as base polymer for sealants applied to fill the joints in pavement, insulation glass units, and aircraft structures.

Polysulfide polymers are conventionally synthesized by condensation polymerization reactions between organic dihalides and alkali metal salts of polysulfide anions:

n Na$_2$S$_x$+n ClCH$_2$CH$_2$OCH$_2$OCH$_2$CH$_2$Cl→
[CH$_2$CH$_2$OCH$_2$OCH$_2$CH$_2$S$_x$]$_n$+2n NaCl

Dihalides used in this condensation polymerization are dichloroalkanes (such as 1,2-dichloroethane, bis-(2-chloroethyl)formal (ClCH$_2$CH$_2$OCH$_2$OCH$_2$CH$_2$Cl), and 1,3-dichloropropane). The obtained macromolecules are then usually reduced to the required chain length by reductive splitting. The split disulfide groups are converted into reactive terminal thiol groups.

The above process produces salt as by-product. Salt wastes are evidently undesired, resulting in a search for salt-free production processes.

A salt-free process is presented in US 2007/0249860, which discloses a process for the preparation of hydroxyalkyl-terminated polysulfides by reacting monomeric hydroxyalkyl terminated polysulfides, in particular dithioglycols, with formaldehyde in the presence of an acid catalyst:

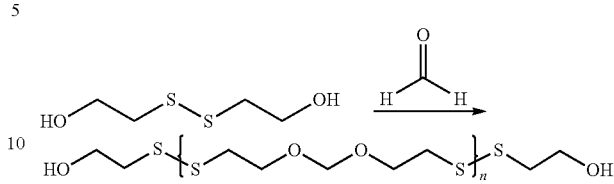

The resulting hydroxyalkyl-terminated polysulfides, however, cannot be applied in systems that are based on oxidative curing methods. This is in contrast to mercapto-terminated polysulfides, which are more reactive under these conditions. Preparing mercapto-terminated polysulfides by transforming the hydroxy end-groups of the above polymers into mercapto end-groups in high yields is troublesome, if possible at all. High conversions are difficult to attain, because the risk of chain scission is high. Furthermore, the transformation involves the formation of inorganic salts, which have to be washed out.

Another way to prepare mercapto-terminated polysulfides is by oxidative polymerization of bismercaptodiethers. An example of an oxidizing agent is elemental sulfur, as disclosed in CA 832049. The process according to this document is performed in the presence of a basic catalyst and, preferably, in the absence of solvent. Although not preferred, chloroform, carbon tetrachloride, benzene, toluene, or xylene, are disclosed as suitable solvents for use in this process.

The oxidation of bismercaptoethers (like the one of formula 1 below) can result in many different polysulfides, for instance linear di-sulfides (formula 2), cyclic disulfides (formula 3), linear tri-sulfides (formula 4), cyclic tri-sulfides (formula 5), linear tetra-sulfides (formula 6), cyclic tetra-sulfides (formula 7), etc.:

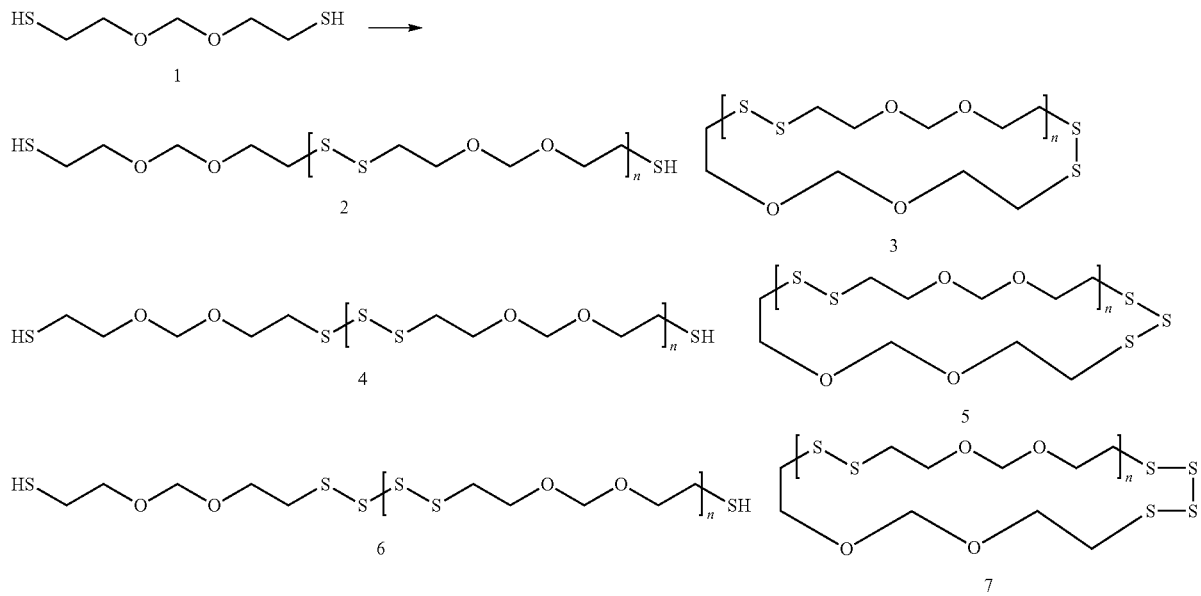

Of these possible structures, linear di-sulfides are liquid and have the highest flexibility and are therefore the preferred structures for sealant applications. Furthermore, compared to tri-, tetra, or other poly-sulfides, linear di-sulfides show good application properties, such as a sufficient pot-life. The other polysulfides are too reactive for convenient handling.

It has now been found that the selectivity of the oxidation of towards linear di-sulfides can be improved by performing the oxidation of bismercaptoether with elemental sulfur in the presence of a base and a protic solvent.

Therefore, the present invention relates to a process for the preparation of polysulfide of formula (I):

$$HS-(CH_2)_n-O-(CH_2)_m-O-(CH_2)_p-[S-S-(CH_2)_n-O-(CH_2)_m-O-(CH_2)_p]_q-SH \quad (I)$$

wherein m is an integer in the range 1 to 4, n and p are integers in the range 1-10, and q is an integer in the range 1-60, by oxidizing a bismercaptodiether compound of formula (II):

$$HS-(CH_2)_n-O-(CH_2)_m-O-(CH_2)_p-SH \quad (II)$$

wherein m, n, p, and q are as defined above, with elemental sulfur in the presence of an alcoholic solvent.

Examples of suitable protic solvents are water and alcohols. Alcohols are the preferred protic solvents. Examples of suitable alcohols are methanol, ethanol, isopropanol, n-propanol, butanols, pentanols, glycol and mixtures thereof. Methanol is the most preferred solvent due to its availability and ease to use.

The bismercaptodiether to be oxidized in the process according to the present invention has the formula $$HS-(CH_2)_n-O-(CH_2)_m-O-(CH_2)_p-SH$$

wherein m is an integer in the range 1 to 4, preferably 1, and n and p are integers in the range 1-10, preferably in the range 1-6, and most preferably 2. Hence, the most preferred bismercaptodiether is bis(mercaptoethoxy)methane.

The base that is present during the reaction serves as a catalyst. The base can be an organic base or an inorganic base. Examples of organic bases are amines and quaternary ammonium compounds.

Examples of suitable amines are mon-, di- and tertiary amines, such as methylamine, ethylamine, propylamine, isopropylamine, butylamine, isobutylamine, pentylamine, triethylamine, tributylamine, ethylenediamine, sec-butylamine, tert-butylamine, methylethylamine, dimethyl-sec-butylamine, aniline, N-methylaniline, N,N-dimethylaniline, γ-aminobutyric acid, 2-aminoethanol, 2,4,6-tribromoaniline, N-methyl-N-ethylaniline, p-nitroso-N,N-dimethylamine, p-toluidine, cyclohexylamine, benzylamine, hexamethylenediamine, benzidine.

Examples of quaternary ammonium compounds are tetramethylammonium hydroxide, tetraethylammonium hydroxide, tetrapropylammonium hydroxide, tetramethylammonium bisulfide, tetraethylammonium bisulfide.

Examples of inorganic bases are lithium hydroxide, sodium hydroxide, potassium hydroxide, calcium hydroxide, magnesium hydroxide, sodium bicarbonate, sodium carbonate, potassium bicarbonate, potassium carbonate, sodium oxide, magnesium oxide, calcium oxide, calcium carbonate, sodium phenoxide, sodium bisulfide, sodium sulfide, potassium bisulfide, potassium sulfide, barium phenoxide, calcium phenoxide, RONa, RSNa, and mixtures of any two or more thereof; where R can be a $C_1$-$C_{18}$ alkyl radical.

As inorganic base sodium hydroxide is preferred due to its availability and low cost, while triethylamine as organic base is preferred due to its availability and ease to work up.

The base is preferably used in the process of the present invention in an amount of 0.1-10 mol %, more preferably 0.2-6.0 mol %, and most preferably 0.4-3.2 mol %, relative to the bismercaptodiether.

The molar ratio elemental sulfur to bismercaptodiether preferably ranges from 0.5:1 to 1.2:1, more preferably from 0.6:1 to 1.1:1, and most preferably from 0.7:1 to 0.99:1. The higher this ratio, the longer the chain length (q) of the resulting polysulfide.

The amount of solvent used for the reaction is a wide extent, depending on the available process equipment, the convenience of industry operation and the costs in involved. Based on 1 g of the bismercaptodiether, the amount of solvent is preferably in the range of 0.2-100 ml, more preferably 0.5-20 ml.

Generally, high amounts of solvent promote the formation of higher molecular weight polysulfides and reduced amounts of trisulfides and cyclic disulfides.

The process according to the present invention is preferably performed under inert, e.g. nitrogen, atmosphere. Bubbling of inter gas through the reaction mixture enables the removal of formed $H_2S$ and thereby the shift of the reaction equilibration towards the polysulfide.

The process is preferably performed at a temperature ranging from room temperature to the boiling point of the solvent, more preferably in the range 60-85° C.

The process is generally conducted for 4-24 hours, more preferably 5-12 hours, and most preferably 6-8 hours. If the process is conducted for less than about 4 hours, considerable amounts of trisulfides and tetrasulfides were detected.

The resulting polysulfide is a disulfide with the formula $$HS-(CH_2)_n-O-(CH_2)_m-O-(CH_2)_p-[S-S-(CH_2)_n-O-(CH_2)_m-O-(CH_2)_p]_q-SH$$

wherein m is an integer in the range 1 to 4, preferably 1, n and p are integers in the range 1-10, preferably in the range 1-6, and most preferably 2, and q is an integer in the range 1-60, preferably 3-50, and most preferably 5-35.

This polysulfide can be isolated from the reaction mixture by any suitable method, depending on the other compounds present in the reaction mixture. Examples of suitable separation methods are decantation and high vacuum evaporation (e.g. when a low boiling base is used) or filtration (e.g. when using an inorganic base like NaOH).

Washing and neutralization steps may be performed, but are not essential.

The resulting polysulfide has various applications, including the use as binder in sealants, adhesives, and coating compositions, in isocyanate cure, in epoxy-resin cure, and in acrylated resin cure.

EXAMPLES

Example 1

To a 500 ml, 3-necked flask equipped with a thermowell, mechanical stirring bar, $N_2$ input tube, and condenser was added 25 g bis(mercaptoethoxy)methane, 10 ml methanol, and 0.1 ml triethyl amine. To the resulting mixture, 4.8 g sulfur powder was added in two portions. The mixture was heated to 60° C. and maintained at 60° C. for 4 hours. After that, the mixture was cooled down to room temperature and the oil layer was separated from the aqueous layer and concentrated to obtain a pale yellow oil (21.1 g).

This pale yellow oil was analyzed by $^1H$ NMR, $^{13}C$ NMR, LC, GPC, and IR. These methods showed the formation of linear disulfides and no trisulfides.

Comparative Example A

To a 25 ml, 3-necked flask equipped with a thermowell, mechanical stirring bar, $N_2$ input tube, and condenser was added 0.5 g bis(mercaptoethoxy)methane, 10 ml THF, and 13 µl triethyl amine. To the resulting mixture, 0.09 g sulfur was added in one portion. The mixture was heated up to 60° C. and maintained at 60° C. for 24 hours. After that, the mixture was cooled down to room temperature and the oil layer was separated from the aqueous layer and concentrated to obtain a pale yellow oil (0.46 g).

This pale yellow oil was analyzed by $^1$H NMR, $^{13}$C NMR, LC, GPC, and IR. These methods showed a ratio between disulfides and trisulfides in the oil of almost 1:1.

Comparative Example B

Bis(mercaptoethoxy)methane (0.5 g) in DMSO (1 ml) was kept at 98° C. for 8 hours. After cooling down, the mixture was extracted with toluene (50 mL); three times. The toluene layer was then washed with water (50 ml) twice. The organic layer was concentrated to afford a pale yellow oil (0.31 g).

This pale yellow oil was analyzed by $^1$H NMR, $^{13}$C NMR, LC, GPC, and IR. These methods showed the formation of linear disulfides together with a considerable amount of polymers with unreactive terminal groups.

Comparative Example C

Oxygen (air) was bubbled into the mixture of bis(mercaptoethoxy)methane (0.4 g) and Al$_2$O$_3$ (2 g) in toluene (2 ml) at room temperature. After 3 days, a sample was taken out for analysis. $^1$H NMR showed that the major component in the product was still monomer. After 8 days, solid was filtered out, and it was washed with toluene (10 ml); three times. The toluene layer was concentrated to afford a pale yellow oil (0.25 g).

This pale yellow oil was analyzed by $^1$H NMR, $^{13}$C NMR, LC, GPC, and IR. These methods showed that cyclic disulfides together with OH-terminated polymers were formed.

Comparative Example D

Bis(mercaptoethoxy)methane (0.5 g) in H$_2$O (3 ml) was heated up to 60° C. H$_2$O$_2$(30% in H$_2$O, 0.27 ml) in H$_2$O (3 ml) was added dropwise in 10 min. After 1 hr, the mixture was cooled down and Na$_2$S$_2$O$_3$ (1% in H$_2$O, 8 ml) was added. The mixture was extracted with toluene (50 ml)—three times—followed by concentration to afford a pale yellow oil (0.37 g).

This pale yellow oil was analyzed by $^1$H NMR, $^{13}$C NMR, LC and IR. These methods showed the formation of linear disulfides together with a considerable amount of monomers as well as some unknown impurities. Longer reaction time led to more unknown by-products.

The invention claimed is:

1. A process for the preparation of polysulfide of formula (I)

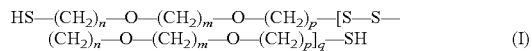

wherein m is an integer in the range 1 to 4, n and p are integers in the range 1-10, and q is an integer in the range 1-60,
by oxidizing a bismercaptodiether compound of formula (II)

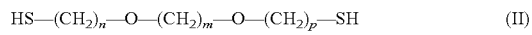

with elemental sulfur in the presence of a base and a protic solvent.

2. The process according to claim 1 wherein m=1.

3. The process according to claim 1 wherein n=p=2.

4. The process according to claim 1 wherein the protic solvent is an alcohol.

5. The process according to claim 4 wherein the alcohol is methanol, ethanol or isopropanol.

6. The process according to claim 1 wherein the base is a quaternary ammonium compound, a tertiary amine, or an inorganic base.

7. The process according to claim 6 wherein the base is triethylamine or NaOH.

8. The process according to claim 1 wherein the molar ratio elemental sulfur:bismercaptoether is in the range 0.5:1 to 1.2:1.

9. The process according to claim 8 wherein the molar ratio elemental sulfur:bismercaptoether is in the range 0.7:1 to 0.99:1.

10. The process according to claim 1 wherein the process is performed at a temperature in the range 60-85° C.

11. A process for the preparation of a liquid polysulfide of formula (I)

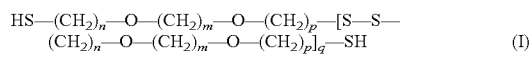

wherein m is an integer in the range 1 to 4, n and p are integers in the range 1-10, and q is an integer in the range 1-60,
by oxidizing a bismercaptodiether compound of formula (II)

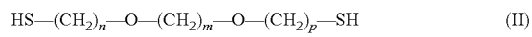

with elemental sulfur in the presence of a base and a protic solvent.

* * * * *